United States Patent
Anderson et al.

(10) Patent No.: US 10,095,197 B1
(45) Date of Patent: Oct. 9, 2018

(54) COGNITIVE PLANT CLINIC

(71) Applicant: INTERNATIONAL BUSINESS MACHINES CORPORATION, Armonk, NY (US)

(72) Inventors: Evelyn R. Anderson, Houston, TX (US); Natalie N. Brooks Powell, Bolingbrook, IL (US); Kristen N. Conley, Kieler, WI (US); Martin G. Keen, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/820,654

(22) Filed: Nov. 22, 2017

Related U.S. Application Data

(63) Continuation of application No. 15/632,687, filed on Jun. 26, 2017.

(51) Int. Cl.
*G05B 13/02* (2006.01)
*G05B 23/02* (2006.01)

(52) U.S. Cl.
CPC ......... *G05B 13/028* (2013.01); *G05B 23/021* (2013.01); *A01N 2300/00* (2013.01); *G05B 23/0272* (2013.01); *G05B 2219/31472* (2013.01)

(58) Field of Classification Search
CPC ............................ G05B 13/082; G05B 23/021; G05B 23/0272; A01N 2300/00
USPC .................................................. 340/3.4–3.44
See application file for complete search history.

(56) References Cited

U.S. PATENT DOCUMENTS

| | | | |
|---|---|---|---|
| 5,149,624 A | 9/1992 | Gabriel | |
| 6,014,451 A | 1/2000 | Berry et al. | |
| 9,380,747 B2 * | 7/2016 | Sasaki | A01G 7/00 |
| 2016/0171407 A1 | 6/2016 | Jagyasi et al. | |

FOREIGN PATENT DOCUMENTS

| | | |
|---|---|---|
| CN | 102945376 | 3/2016 |
| DE | 202016004430 | 9/2016 |
| JP | 2016168046 | 9/2016 |
| WO | WO 1998021571 | 5/1998 |

OTHER PUBLICATIONS

E. Anderson, et al., "Cognitive Plant Clinic" U.S. Appl. No. 15/632,687, filed Jun. 26, 2017.

(Continued)

*Primary Examiner* — Allen T Cao
(74) *Attorney, Agent, or Firm* — Robert J. Shatto, Esq.; George S. Blaisak, Esq.; Heslin Rothenberg Farley & Mesiti, P.C.

(57) ABSTRACT

Methods, computer program products, and systems are presented. The methods include, for instance: obtaining an input including an image of a plant, identifying a species of the plant by use of visual recognition of the image. The image is analyzed for symptoms and candidate diagnoses are selected from a diagnostic repository according to the symptoms. With respective candidate diagnoses, a confidence score and a treatment regimen are associated. According to a treatment mode, the candidate diagnoses and treatment regimen are delivered.

7 Claims, 4 Drawing Sheets

(56) References Cited

OTHER PUBLICATIONS

List of IBM Patent and/or Patent Applications treated as related for U.S. Appl. No. 15/820,654, filed Nov. 22, 2017, dated Nov. 22, 2017.
Mell, P., et al. "The NIST Definition of Cloud Computing" NIST Special Publication 800-145, Gaithersburg, MD (Sep. 2011).
Notice of Allowance for U.S. Appl. No. 15/632,687, filed Jun. 26, 2017, dated May 23, 2018.
Applicant's Amendment under 37 CFR 1.312 in U.S. Appl. No. 15/632,687, filed Jun. 26, 2017, dated Jun. 13, 2018.
Applicant's Comment on Statement of Reasons for Allowance in U.S. Appl. No. 15/632,687, filed Jun. 26, 2017, dated Jun. 14, 2018.

\* cited by examiner

COGNITIVE PLANT CLINIC

CROSS-REFERENCE TO RELATED APPLICATION

This application is a continuation of U.S. patent application Ser. No. 15/632,687, filed Jun. 26, 2017, entitled, "Cognitive Plant Clinic," the entirety of which is hereby incorporated herein by reference.

TECHNICAL FIELD

The present disclosure relates to cognitive computing and visual recognition technologies, and more particularly to methods, computer program products, and systems for providing clinical services for caretakers of plants.

BACKGROUND

Conventionally horticultural application of digital technology has been limited, and when horticulturists encounter abnormalities on plants under their care, seeking help from a local expert would have been a matter of course.

SUMMARY

The shortcomings of the prior art are overcome, and additional advantages are provided, through the provision, in one aspect, of a method. The method for providing a clinical service for plants includes, for example: obtaining, by one or more processor, an input including an image of a plant from a camera, as configured by a user caring for the plant; identifying, by the one or more processor, a species of the plant by use of visual recognition of the image; producing, by the one or more processor, a list of one or more candidate diagnosis for the species by correlating one or more visual symptom of the plant with one or more known diagnosis recorded in a diagnostic repository, and by associating each of the one or more candidate diagnosis with a respective confidence score according to the input; mapping, by the one or more processor, each of the one or more candidate diagnosis in the list to a respective treatment regimen; and delivering, by the one or more processor, the list and the respective treatment regimen mapped to each candidate diagnosis in the list, according to a treatment mode as preconfigured.

Additional features are realized through the techniques set forth herein. Other embodiments and aspects, including but not limited to computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
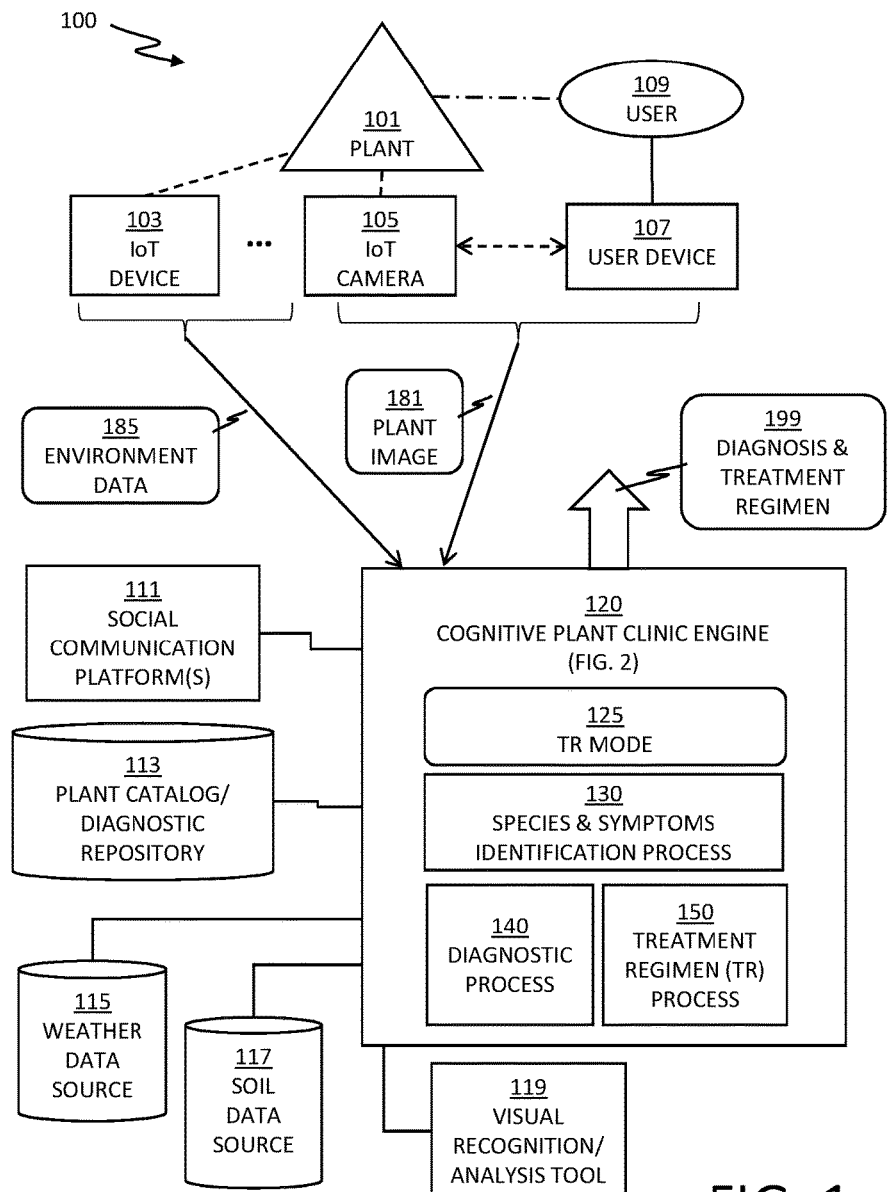
FIG. 1 depicts a system 100 for providing plant diagnosis and treatment services, in accordance with one or more embodiments set forth herein.

FIG. 1 depicts a system 100 for providing plant diagnosis and treatment services, in accordance with one or more embodiments set forth herein.

Gardening is one of the most popular pastime as well as a promising business opportunity. Particularly for hobbyist gardeners, taking care of diseased plants without the help of an expert might be difficult because there are many symptoms indistinguishable for non-experts, because there are many plant species and subspecies that have respective symptoms and treatments even for a same disease, and because there are many varieties of diseases that are caused by distinctive reasons divided into biotic causes indicating pathogens, and abiotic causes indicating environmental factors. Accordingly, it would be desirable to correctly identify a plant species of a plant, to accurately identify the symptoms and diagnose a disease for the plant species, and to properly treat the plant for the disease.

The system 100 provides the plant species identification, diagnoses based on visual symptoms, and treatment services to a user 109 who takes care of a plant 101. The plant 101 may be located in an environment that may be specified by use of many factors, including, but not limited to, an indoor/outdoor, hours of sun/shade, light sources, air flows for indoor environments and wind speed for outdoor environments, a level of moisture in the air/soil, soil compositions, etc.

The system 100 includes a cognitive plant clinic engine 120. An Internet of Things (IoT) device 103 is one of many IoT devices operatively coupled to the cognitive plant clinic engine 120. The IoT device 103 monitors and/or controlled the environment of the plant 101. Examples of the IoT device 103 may include, but are not limited to, thermostats, thermometers, plant grow lightings, air conditioners, air speed indicators including anemometers, air quality sensors, various other weather instruments various horticultural equipment such as hydroponic grower containers, etc. Accordingly, the IoT device 103 captures a type of environment data 185 of the plant 101 corresponding to functionalities of the IoT device 103 and sends the environment data 185, along with other IoT devices associated with the plant 101, to the cognitive plant clinic engine 120.

The user 109 takes a picture of the plant 101 with an IoT camera 105 in order to capture a plant image 181, upon noticing a certain visual abnormality on the plant 101, or to figure out whether or not the plant 101 is free of any disease. The IoT camera 105 may transmit the plant image 181 to the cognitive plant clinic engine 120, directly or via a user device 107. The IoT camera 105 may be a part of the user device 107 by which the user 109 communicates with the cognitive plant clinic engine 120. Examples of the user device 107 may be a smartphone, a laptop, a tablet, etc. Examples of the IoT camera 105 may be a digital camera portion of a smartphone, a standalone digital camera with a communication functionality via various networks, etc.

The cognitive plant clinic engine 120 is operatively coupled to various external tools/data sources including one or more social communication platform 111, a plant catalog/diagnostic repository 113, a weather data source 115, a soil data source 117, and a visual recognition/analysis tool 119.

Respective functionalities/data of the external tools 111, 113, 115, 117, and 119 are readily available for the cognitive plant clinic engine 120.

The cognitive plant clinic engine 120 includes configuration data for, among others, a treatment regimen (TR) mode 125, as well as processes such as a species and symptoms identification process 130, a diagnostic process 140, and a treatment regimen (TR) process 150. The species and symptoms identification process 130, the diagnostic process 140, and the treatment regimen (TR) process 150 indicate respective functionalities of the cognitive plant clinic engine 120 and may or may not be implemented as separate processes. The cognitive plant clinic engine 120 processes the plant image 181 and the environment data 185 according to the operations presented in FIG. 2 and corresponding descriptions. As a result, the cognitive plant clinic engine 120 generates and/or performs a diagnosis and treatment regimen 199 and reports to the user 109, of which details are presented in FIG. 2 and corresponding descriptions.

Figure 2:
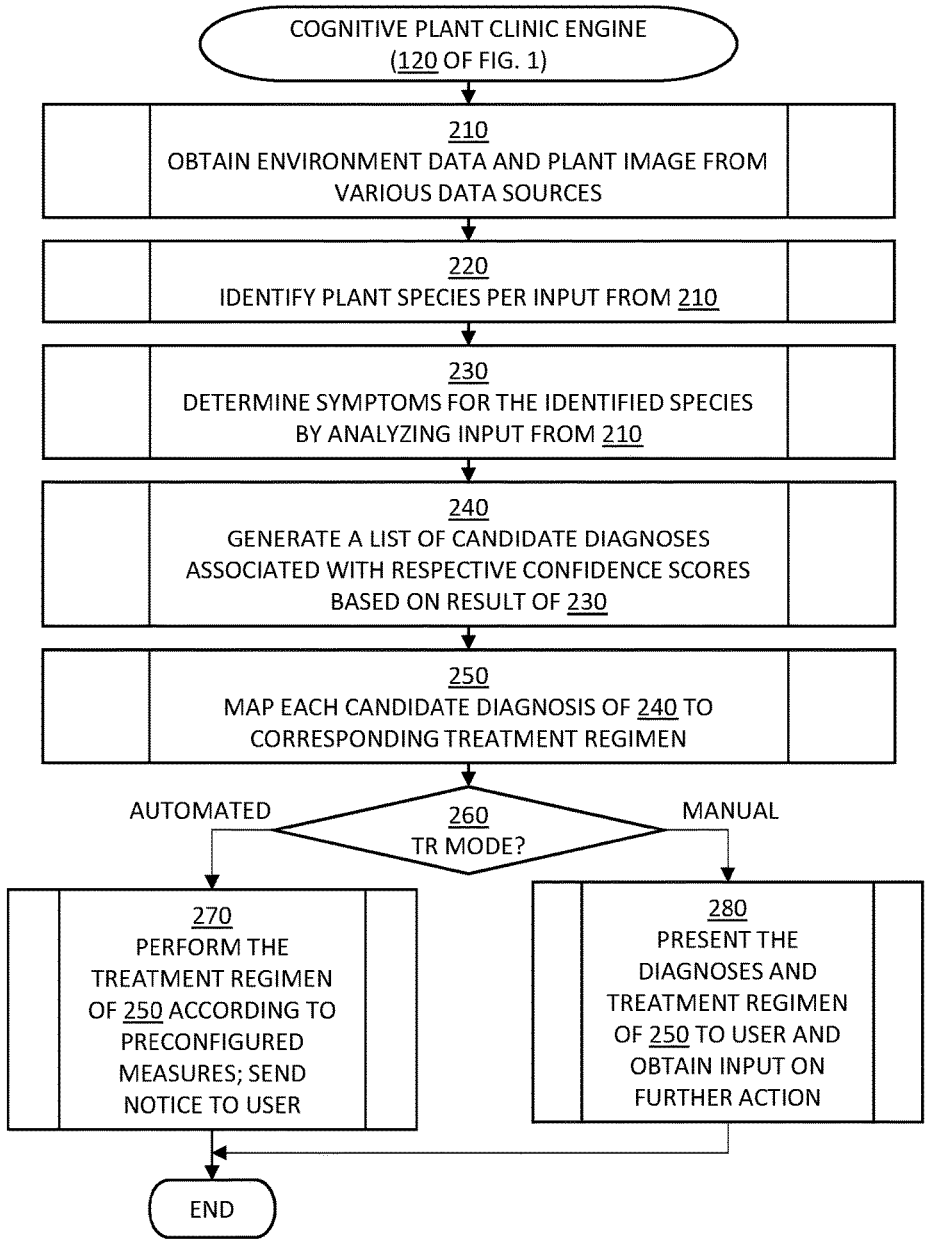
FIG. 2 depicts a flowchart performed by the cognitive plant clinic engine of the system, in accordance with one or more embodiments set forth herein.

FIG. 2 depicts a flowchart performed by the cognitive plant clinic engine 120 of FIG. 1, in accordance with one or more embodiments set forth herein.

Blocks of FIG. 2 indicate respective operational phases for the cognitive plant clinic engine 120, which may or may not be implemented as separate processes. Each block in FIG. 2 may include multiple processes, subprocesses and/or operations, including involving one or more external tool by sending a request and by receiving a result responsive to the request.

In block 210, the cognitive plant clinic engine 120 obtains environment data and a plant image data from IoT devices and/or a user device, responsive to monitoring the plant and sending the data. Then the cognitive plant clinic engine 120 proceeds with block 220.

In certain embodiments of the present invention, the IoT camera may be configured to send, upon being manually captured by a user, the plant image to the cognitive plant clinic engine 120. In certain embodiments of the present invention, the IoT camera may be configured to send multiple plant images as a batch to the cognitive plant clinic engine 120. In certain embodiments of the present invention, the IoT camera may be configured to capture and to send one or more plant image periodically at least once a predefined exam period. The IoT camera may be a separate camera device, and/or one of many functionalities of the user device, such as a camera in a smartphone. In certain embodiments of the present invention, the plant image may be in an Exchangeable image file format (Exif). In certain image file formats, the plant image may be embedded with metadata such as a geographical location and a timestamp, the geographical location indicating at which location/address/coordinates the plant image has been taken, the timestamp indicating on which date and time the plant image has been captured.

In block 220, the cognitive plant clinic engine 120 identifies the species of the plant 101 as captured in the plant image by comparing the plant image with content of the plant catalog associating visual features with corresponding plant species. The cognitive plant clinic engine 120 may further make use of the environment data input from block 210 in determining the species and/or differentiating similar species. Then the cognitive plant clinic engine 120 proceeds with block 230.

In certain embodiments of the present invention, the cognitive plant clinic engine 120 may utilize external visual recognition utilities and/or image analysis tools in identifying the plant specifies by analyzing visual features of the plant and by comparing visual features of plants listed in the plant catalog. In certain embodiments of the present invention, the cognitive plant clinic engine 120 may utilize the geographical location data and the timestamp in identifying outdoor plants, in combination with climate/soil data for the geographical location and weather records at the date and time from the timestamp, in order to narrow down the candidate plant species. The cognitive plant clinic engine 120 may consider characteristics of respective plant species as to the climate habitability, soil compositions, seasonal growth patterns, etc., in identifying the plant species. The cognitive plant clinic engine 120 determines the species of the plant as one of a candidate species that is associated with the highest probability, which is assigned to the identified species as a confidence score indicating how likely the plant captured in the plant image may be the identified species.

In block 230, the cognitive plant clinic engine 120 determines symptoms for the identified species from block 220 by analyzing the input from block 210. The cognitive plant clinic engine 120 determines what types of abnormalities on which parts of the plant, in specifying each symptom. Examples of abnormalities on the plant may include, but are not limited to, spots, lesions, discoloration including chlorosis, wilting/withering, rotting, deformation, etc. Examples of plant parts may include, but are not limited to, a root, a stem, a leaf blade, a petiole/leafstalk, a flower, a seed/fruit, a leaf bud, a flower bud, etc., and combinations thereof. Then the cognitive plant clinic engine 120 proceeds with block 240.

In certain embodiments of the present invention, the cognitive plant clinic engine 120 performs an analysis on the plant image from block 210 by use of an external visual recognition/analysis tool. The cognitive plant clinic engine 120 compares the symptoms shown in the plant image against symptoms images with known diagnoses as recorded in the plant catalog/diagnostic repository. The cognitive plant clinic engine 120 may also compare the plant image against the symptoms images for the same species as the identified species for the plant image as well as other species that may share a propensity to a certain disease with the identified specified of the plant image, as symptoms of such other species may be indicative of a same diagnosis for the identified species of the plant image. The cognitive plant clinic engine 120 may also compare the season of the year, the location of the plant, against the date and location metadata of the symptoms images in the plant catalog/diagnostic repository. The cognitive plant clinic engine 120 tracks similarities in the respective seasons and locations of the images in the diagnostic repository and the plant image in order to account the similarities into a confidence score corresponding to a diagnosis for the plant image. As the cognitive plant clinic engine 120 may discover a plurality of images of symptoms with known diagnoses, the cognitive plant clinic engine 120 utilizes the confidence score in order to determine the most likely diagnosis for the plant image.

In certain embodiments of the present invention, the cognitive plant clinic engine 120 may further analyze reference images posted on social media (SM), which include a plant of the same species as the identified species of the plant image and/or have similar visual symptoms. The cognitive plant clinic engine 120 sends a query to the social media for posted images that include the plant species with similar visual characteristics, having similar visual symptoms, by use of the visual recognition/analysis tool. The cognitive plant clinic engine 120 sends the plant image to the visual recognition/analysis tool, which derives textual classifiers from the features of the plant image such as a name of the plant, description of the symptoms shown in the plant image, etc. The cognitive plant clinic engine 120 queries the social media with terms equivalent to the textual classifiers, by which the social media searches images posted on the social media platform. Certain social media platforms may search captions and tags associated with SM-posted images. When a partial match is discovered as textual description does not have sufficient detail for determining a full match to the plant species and the visual symptoms, the social media platform may respond to the cognitive plant clinic engine 120 with the SM-posted image. The cognitive plant clinic engine 120 subsequently may further analyze the partially matching SM-posted image by use of the visual recognition/analysis tool as in the analysis of the plant image, in order to derive full textual classifiers describing the SM-posted image. If the cognitive plant clinic engine 120 discovers that the textual classifiers of the plant image are identical to the textual classifiers of the SM-posted image, then the cognitive plant clinic engine 120 determines that the SM-posted image is usable as a reference image for various comparisons to the plant image, and for adjusting the confidence scores associated with species identification and diagnoses.

The cognitive plant clinic engine 120 then checks for similarities in the visual symptoms to the plant image, as well as metadata including date and location. Further, the cognitive plant clinic engine 120 may take comments and discussions regarding the visual symptoms in the SM-posted images into consideration as the comments may be relevant to the diagnosis, a geographical range of the symptoms, a particular supplier of the plant, opinions by other plant caretakers, etc., which may contribute to the diagnosis as well as a discovery of the cause of the visual symptoms for the plant image from block 210. Similarly with the visual symptoms images, the cognitive plant clinic engine 120 tracks similarities in the respective seasons and locations of the SM-posted images with the plant image, and increases the confidence score corresponding to a diagnosis for the plant image, as the same diagnosis for the SM-posted image in close proximity in time and location supports the diagnosis for the plant image.

In block 240, the cognitive plant clinic engine 120 generates a list of candidate diagnoses, which are respectively associated with a confidence score based on the visual symptoms specified in block 230 for the identified species. The cognitive plant clinic engine 120 searches the plant catalog/diagnostic repository for one or more name corresponding to respective plant diseases that may have caused the visual symptoms specified from block 230. The cognitive plant clinic engine 120 includes the one or more plant diseases names discovered as having matching visual symptoms in the list of candidate diagnoses. Examples of plant diseases may include, but are not limited to, anthracnose/canker, blight, diebacks, wilt disease, root rots, crown gall, etc. Certain visual symptoms may be easily correlated to a certain plant disease, and to biotic and/or abiotic causes, and some other visual symptoms may be common to many plant diseases. Biotic causes of the plant diseases are typically fungi and bacteria transmitted by insects. Abiotic causes of the plant diseases may be environmental factors such as drought, nutrient deficiencies, extreme temperatures, soil moisture levels, pollution, etc.

The cognitive plant clinic engine 120 assesses respective confidence scores associated with each diagnosis in the list of candidate diagnoses based on factors indicating how closely the plant image may be related to a reference image demonstrating the similar visual symptoms. Examples of the confidence score factors may be, but are not limited to, geographical and temporal proximities, compatibilities with climates, temperatures, and/or seasons, a number of confirmed identical diagnoses in the area, a number of reports on the identical diagnosis via the social media, the level of similarity between the plant image and images of confirmed diagnoses, other conditions of the plant image satisfying terms of confirmed diagnoses, etc., and any evidences supporting or negating the diagnosis of the plant image based on the reference image. The cognitive plant clinic engine 120 may further check the diagnosis against weather data and soil data for the geographical origin of the plant image, as such abiotic environmental factors of precipitations, soil compositions, etc., may be indicative of certain causes of the visual symptoms. The cognitive plant clinic engine 120 may increase the confidence score of the diagnosis when evidences supporting the diagnosis are detected, and may decrease the confidence score of the diagnosis when evidences negating the diagnosis are discovered. The cognitive plant clinic engine 120 may further verify the candidate diagnoses by use of user feedback, etc. The cognitive plant clinic engine 120 may update the plant catalog/diagnostic repository with the species identification and the diagnoses associated with a confidence score higher than a threshold value.

For example, if a diagnosed plant disease is known to be caused by a certain insect spreading a certain type of bacteria, then the cognitive plant clinic engine 120 would increase the confidence score of the diagnosis when the same type of insect is observed, captured in images searchable by the cognitive plant clinic engine 120 within a certain geographical boundary from the origin of the plant image.

As noted in block 230, the cognitive plant clinic engine 120 may also adjust the confidence score of a candidate diagnosis based on analyzing the visual symptoms in the SM-posted images. The cognitive plant clinic engine 120 may give more weight to a reference image from the plant catalog/diagnostic repository than another reference image from a social media as acquired from block 230, in comparing environmental relevancies, including geographical locations, climates, and/or seasons, between the respective symptoms from the plant image and the reference image.

In block 250, the cognitive plant clinic engine 120 maps each candidate diagnosis in the list of the candidate diagnoses to zero or more corresponding treatment regimen. In certain embodiments of the present invention, the treatment regimens corresponding to candidate diagnoses may be included in the plant catalog/diagnostic repository, indexed by each disease name. Then the cognitive plant clinic engine 120 proceeds with block 260.

In certain embodiments of the present invention, the cognitive plant clinic engine 120 may map a diagnosis of a plant disease to a fungicide treatment, as the plant disease is known to be caused by insects carrying a type of fungus. The cognitive plant clinic engine 120 may map another diagnosis of another plant disease to a certain care regimen regarding watering, soil nutrients, lighting, and/or ventilation, as the plant disease is known to be caused by environmental conditions.

In block 260, the cognitive plant clinic engine 120 determines a present configuration of a treatment mode of the cognitive plant clinic engine 120. The cognitive plant clinic engine 120 preconfigures the treatment mode according to user input, available IoT devices and respective functionalities, and other information/utility necessary to perform respective treatment modes. For example, in certain embodiments of the present invention, the cognitive plant clinic engine 120 may configure the treatment mode with one instance from {Automated, Manual}. If the cognitive plant clinic engine 120 determines that the treatment mode is presently configured for an automated treatment, then the cognitive plant clinic engine 120 proceeds with block 270. If the cognitive plant clinic engine 120 determines that the treatment mode is presently configured for a manual treatment, then the cognitive plant clinic engine 120 proceeds with block 280.

In block 270 wherein the treatment mode is automated, the cognitive plant clinic engine 120 automatically performs the treatment regimen mapped in block 250 according to preconfigured measures for a candidate diagnosis associated with the highest confidence score amongst all confidence scores for respective candidate diagnoses in the list. The cognitive plant clinic engine 120 may have the preconfigured measures as {Placing order for treating substance/equipment}, {Controlling water supply}, {Controlling lighting}, {Controlling temperature}, etc., and combinations thereof, as set by the user beforehand according to available IoT devices and setup of the IoT devices. The preconfigured measures may be scheduled for a certain period of time while treating the plant, during which the cognitive plant clinic engine 120 controls respective IoT devices to perform the treatment regime. The cognitive plant clinic engine 120 sends a notice indicating that a certain preconfigured measure had been performed to the user. Then the cognitive plant clinic engine 120 terminates the service for the plant image obtained in block 210.

In block 280, the cognitive plant clinic engine 120 presents the candidate diagnoses and the treatment regimen mapped in block 250 to the user who submitted the plant image, as the treatment mode is manual. The cognitive plant clinic engine 120 may also present options that may be automatically performed by the cognitive plant clinic engine 120 but had not been configured yet, and facilitate the user to choose an automated treatment mode. Accordingly, the cognitive plant clinic engine 120 may obtain input from the user and continue performing the treatment regimen as directed by the user input. Then the cognitive plant clinic engine 120 terminates the service for the plant image obtained in block 210.

Certain embodiments of the present invention may offer various technical computing advantages, including a clinical diagnosis and treatment service of a plant based on an image of the plant. The image of the plant is visually analyzed for identifying the species of the plant and visual symptoms captured in the image. The determinations of the species and candidate diagnoses are associated with respective confidence scores, which would be adjusted according to evidences examined from the reference images and various aspects of metadata of the reference images. Supporting and/or negating evidences would be reflected to the confidence scores for the species identification and the candidate diagnoses accordingly. Certain embodiments of the present invention may be implemented by use of various Internet of Things (IoT) device as well as other systems in treating the plant according to one of the candidate diagnoses with the highest confidence score, as an automated treatment regimen may be configured for the clinical services provided. Certain embodiments of the present invention may be implemented by use of a cloud platform/data center, and the plant clinic services may be provided as a subscribed service for individual and/or organizational users.

Figure 3:
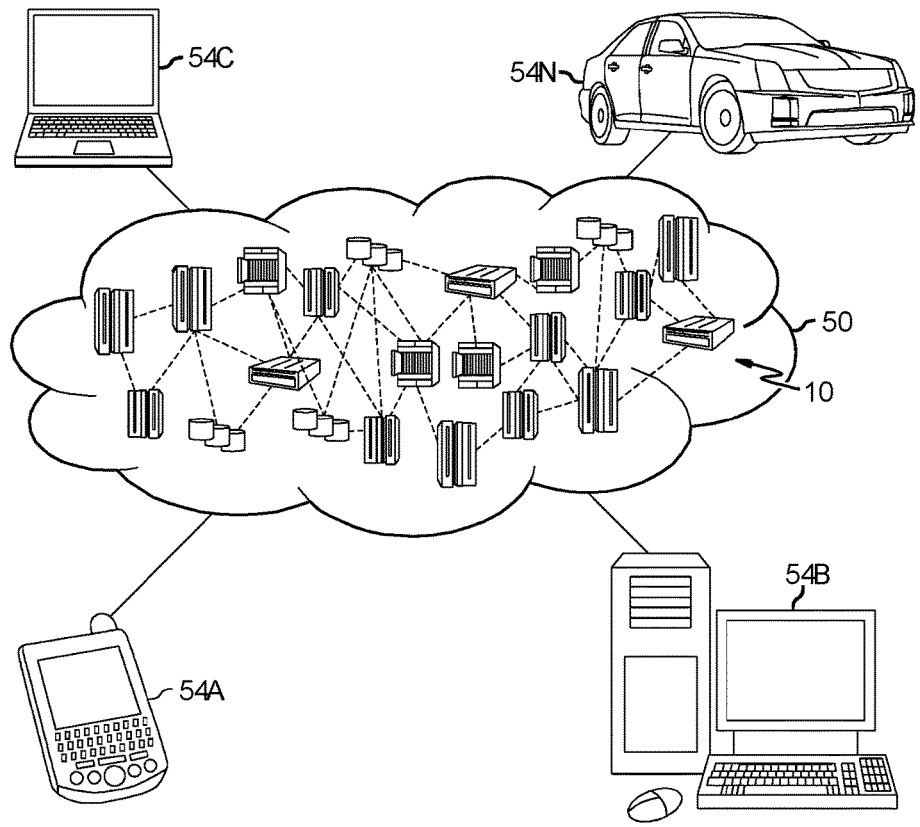
FIG. 3 depicts a cloud computing environment according to an embodiment of the present invention.
Figure 4:
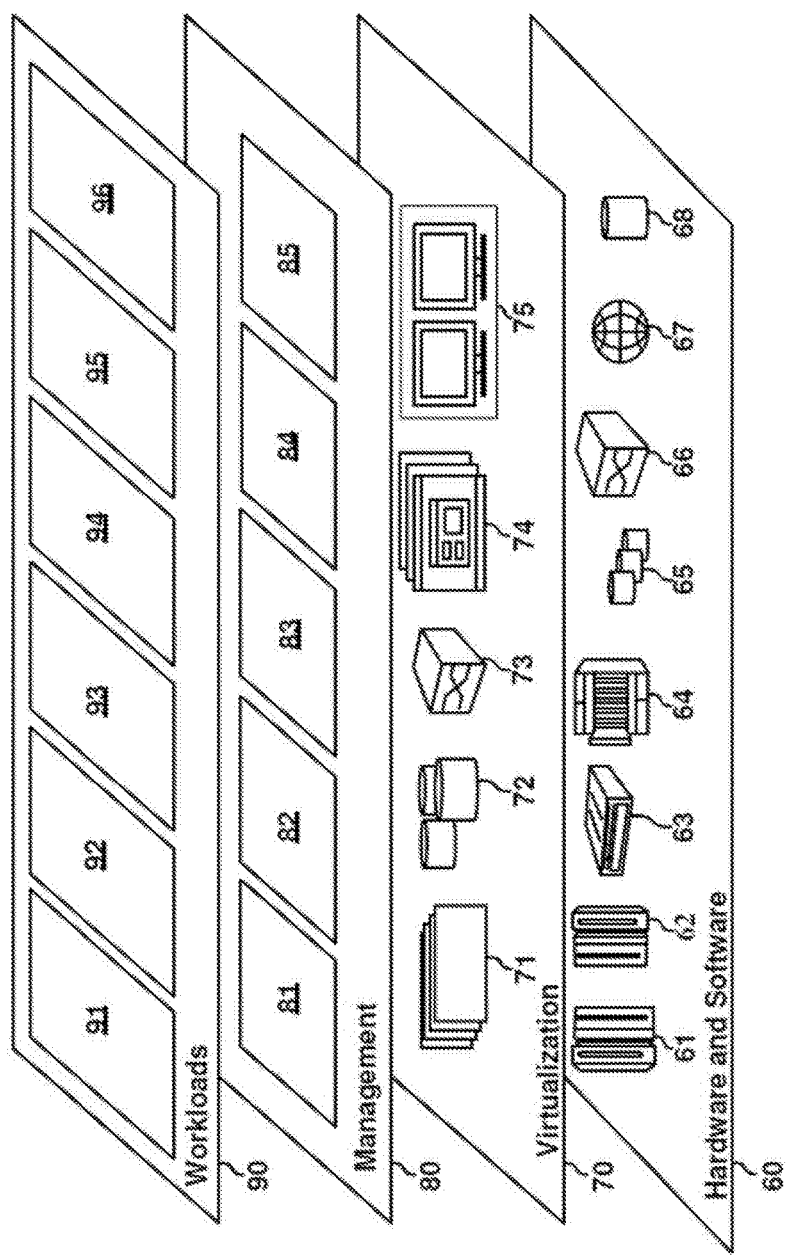
FIG. 4 depicts abstraction model layers according to an embodiment of the present invention.

FIGS. 3-4 depict various aspects of computing, including a cloud computing system, in accordance with one or more aspects set forth herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 3, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Referring now to FIG. 4, a set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components for the cognitive plant clinic engine 96, as described herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method for providing a clinical service for plants, comprising:
    obtaining, by one or more processor, an input including an image of a plant from a camera, as configured by a user caring for the plant;
    identifying, by the one or more processor, a species of the plant by use of visual recognition of the image;
    producing, by the one or more processor, a list of one or more candidate diagnosis for the species by correlating one or more visual symptom of the plant with one or more known diagnosis recorded in a diagnostic repository, and by associating each of the one or more candidate diagnosis with a respective confidence score according to the input;
    mapping, by the one or more processor, each of the one or more candidate diagnosis in the list to a respective treatment regimen; and
    delivering, by the one or more processor, the list and the respective treatment regimen mapped to each candidate diagnosis in the list, according to a treatment mode as preconfigured.

2. The computer implemented method of claim 1, wherein the input includes a geographical location indicating where the image has been taken, a timestamp indicating when the image has been taken, environment data of the plant as reported by one or more device surrounding the plant, other instances of plant images, weather data, soil data, and combinations thereof.

3. The computer implemented method of claim 1, the producing comprising:
    determining the one or more visual symptom of the plant in the image for the species as identified;
    selecting the one or more candidate diagnosis as the one or more known diagnosis from the diagnostic repository, responsive to discovering that the one or more known diagnosis matches the one or more visual symptom of the plant as determined; and
    setting the respective confidence score for each of the one or more candidate diagnosis according to one or more evidence supporting and/or negating each candidate diagnosis.

4. The computer implemented method of claim 3, wherein the one or more known diagnosis includes for the identified species or for other species that are susceptible to the one or more known diagnosis, and wherein the one or more evidence supporting each candidate diagnosis includes a geographical proximity to other instances of the same candidate diagnosis, a similarity in season and/or temperature with said other instances of the same candidate diagnosis.

5. The computer implemented method of claim 1, the delivering comprising:
    determining that the treatment mode is preconfigured as automated;
    selecting a candidate diagnosis with the highest confidence score amongst the one or more candidate diagnosis of the list; and
    performing a treatment regimen corresponding to the candidate diagnosis according to a preconfigured measure.

6. The computer implemented method of claim 5, wherein the preconfigured measure is selected from the group consisting of, Placing order for treating substance/equipment, Controlling water supply, Controlling lighting, Controlling temperature, and combinations thereof.

7. The computer implemented method of claim 1, the delivering comprising:
    determining that the treatment mode is preconfigured as manual;
    communicating the list of the one or more candidate diagnosis and respectively corresponding treatment regimen to the user; and
    performing a treatment regimen as selected by the user, responsive to obtaining a feedback from the user.

* * * * *